United States Patent [19]

Roquet-Jalmar

[11] Patent Number: 4,727,090

[45] Date of Patent: Feb. 23, 1988

[54] PROCESS FOR PREPARING AND THERAPEUTICAL APPLICATIONS OF THE 2,4,6-TRIIODOPHENOL

[75] Inventor: Jorge C. Roquet-Jalmar, Gerona, Spain

[73] Assignee: Bislak, S.A., Gerona, Spain

[21] Appl. No.: 30,940

[22] Filed: Mar. 26, 1987

Related U.S. Application Data

[62] Division of Ser. No. 680,694, Dec. 12, 1984, Pat. No. 4,677,124.

[30] Foreign Application Priority Data

Dec. 16, 1983 [ES] Spain .................................... 528109
Mar. 7, 1984 [ES] Spain .................................... 530343

[51] Int. Cl.$^4$ ............................................. A61K 31/05
[52] U.S. Cl. .................................................... 514/737
[58] Field of Search ........................................ 514/737

[56] References Cited

U.S. PATENT DOCUMENTS 3,182,089  5/1965  Wilbert ............................... 568/323

OTHER PUBLICATIONS

Pharmaceutica Acta. Helvetiae, Nov. 2, 1946, vol. 21, No. 10, pp. 225–228, and translation thereof (Rosenthaler et al).

Primary Examiner—Allen J. Robinson
Attorney, Agent, or Firm—Flynn, Thiel, Boutell & Tanis

[57] ABSTRACT

A method of treating a patient suffering from circulatory cardiovascular diseases which comprises the administration of a therapeutically effective amount of a composition comprising 2,4,6-triiodophenol or pharmacologically acceptable addition salts thereof, in combination with a pharmaceutically acceptable carrier to the patient.

8 Claims, No Drawings

PROCESS FOR PREPARING AND THERAPEUTICAL APPLICATIONS OF THE 2,4,6-TRIIODOPHENOL

This is a division of application Ser. No. 680,694, filed on Dec. 12, 1984, now U.S. Pat. No. 4,677,124.

The present invention relates to 2,4,6-triiodophenol disclosed as a potent antiinflammatory and analgesic and at the same time as a potent antiatherosclerotic, hypocholesteronemic, hypolipemic, vasodilator and fluidifying-aggregate agent.

The 2,4,6-triiodophenol product is a yellowish crystalline powder, with a melting point of 157° C. not very soluble in water, somewhat soluble in organic dissolvents, as the ethylic and propylic alcohols, acetone and sulfuric ether and very soluble in chloroform and dichloromethane. It is also soluble in alkali solutions.

The 2,4,6-triiodophenol is known since many years ago, for instance Rosenthaler, Capuano Pharm. Acta Helv. 21 (1946)-225, but up to now no practical applications in the industrial or commercial field were found.

Therefore, one of the objects of the present invention is the application of the 2,4,6-triiodophenol as a potent and efficacious antiinflammatory and analgesic, specially by parenteral administration, in human as well as in veterinary therapeutic.

The product applied via parenteral administration, at a dosage of 1 mg/kg produces effects which are comparable and even higher than the effects of other classical antirheumatics as the aspirin and indomethacin at therapeutic dosages.

The preferred administration is via parenteral, particularly via intramuscular, but also other ways give quite efficacious results, as oral, rectal and cutaneous administration. Consequently it is also an object of the present invention the therapeutical application of the 2,4,6-triiodophenol, as well as the pharmaceutical compositions containing as active principle the 2,4,6-triiodophenol, associated with excipients specially conceived for the administration in the form of pharmaceutical preparations, and according to each case in the injectable form, tablets, syrups, lotions, suppositories, pomades, collyria, etc.

Another object of the invention is the application of the 2,4,6-triiodophenol in the treatment of cases of cerebral vascular insufficiency, coronary insufficiency and ventricular function hepatic insufficiency and portal hypertension and chronic ischemia of the lower extremities. Parenteral administration is preferred, particularly the intramuscular way, but also other vias are efficacious, as oral and rectal administration, at daily and unit dosages of 0,5 mg/Kg by corporal weight.

Finally it constitutes also an object of the present invention the process for preparing the 2,4,6-triiodophenol, starting from the phenol and iodizing the same directly being of advantage the capacity of the hydrogen peroxide of catalysing the substitution by iodine of the aromatic hydrogens (particularly benzenics) when using a reaction medium which is not very hydrated and acid. The iodization with periodic acid and potassium iodine, in the presence of concentrated sulfuric acid, reveals also very good results.

The following examples illustrate the invention for the process for preparing the product, as well as for the evaluation of its pharmaceutical and pharmacological properties, and for preparing unit dosage forms for therapeutic administration.

EXAMPLE 1

Obtention of the 2,4,6-triiodophenol (a) Direct iodization of the phenol 564 g (6 moles) of phenol and 2284 g (18 equivalents) of iodine, dissolved in 4000 ml methanol are introduced into a reactor of three outlets, provided with a water bath, stirrer, cooler at reflux, thermometer and admixing funnel. 400 ml sulfuric acid was added and the mixture is heated up to 60° C. 900 ml hydrogen peroxide at 30% was added gradually, maintaining the temperature between 60° and 65° C. After the admixing it is under reaction during 4 to 5 hours, maintaining the indicated temperature. Heating is discontinued and the mixture is allowed to stand for 24 hours. The formed precipitate is filtered and vacuum dried. The obtained crude is recrystallized with hot methanol and filtered and washed a methanol/water solution in a ratio of 3/1. About 1250 g of the product was obtained with a melting point of 158°–159° C. (yield: 43/44%). The NMR spectrum, as well as the mass spectrum correspond to 2,4,6-triiodophenol.

(b) Iodization by means of periodic acid/iodide 25,6 g periodic acid (133 moles) was dissolved in 600 ml concentrated sulfuric acid, cooled exteriorly with ice.

55,8 g potassium iodide (336 moles) was added in small portions, and afterwards 12,2 g phenol (128 moles).

The mixture was left during one night under stirring.

It is poured onto ice, the obtained precipitate is filtered and triturated with ethanol to eliminate the excess of iodine.

560 g of pure product (yield: 45%) with features identical to the ones of the product obtained by the former method are obtained by recrystallization in acetone/chloroform.

EXAMPLE 2

Clinical effects with regard to the cardiovascular apparatus

The technology used to show the hemodynamic changes was of the non-invasive type, as in this way experiments can be repeated and are completely innoxious for the patient. Of all the non-invasive methods of diagnosis we selected the most reliable of actual conditions, which is the method of ultrasounds (echo and Doppler's effects). The bidimensional echocardiography in real time, combined with pulsatile Doppler and the bidimensional vascular echography combined with pulsatile Doppler hemodynamic, are actually the two most reliable non-invasive techniques for the study of the anatomic changes and macroscopic hemodynamics with regard to the cardiovascular apparatus. That's why we used for the study of the clinical effects of the 2,4,6-triiodophenol an echo-Doppler trade mark ATL (Mark V), being the transmission frequency of 3 MHz, as well as a continuous Doppler trade mark SONICAID of 4 and 8 MHz.

There have been chosen four vascular territories of our organism:

(1) Cerebral circulation
(2) Intracardiac circulation
(3) Portal-caval circulation
(4) Peripheral circulation in the lower extremities.

Patients were divided in four statistically acceptable groups (50 in each group), comparing the results obtained with this medicament before, during and after the treatment.

Methodologically there are practiced echographical cuts in real time of the heart, big vases, supra-aortic trunks, abdominal aorta, portal and caval systems and iliac and femoral arteries, obtaining fluxmetric samples Doppler in all the mentioned cardiac cavities and blood vessels to study the sense of the flow, outflow (stream) or volume of flow and the hemodynamic features of the sanguineous flow.

All these works disclosed that the 2,4,6-triiodophenol acts onto:

(1) the vascular parietal dynamic of the carotid arteries of already older patients and who present cerebral vascular insufficiency.
(2) The speed of the flow and volume of flow with regard to the primitive and internal carotid arteries, studying the variations which experiments the cerebral circulation in patients with cerebral vascular insufficiency.
(3) The ventricular function in ill persons with dilated-congestive or ischemic cardiopathy, thus showing the intracardiac hemodynamic changes which experiment the precharge, the charge and the post-charge.
(4) The parietal dynamic of the portal system in patients with hepatic insufficiency or portal hypertension.
(5) The speed of hepatic flow and volume of flow measured in the portal system and hepatic artery in the patients as mentioned under (4).
(6) The parietal dynamic of the aortoiliac and iliofemoral sectors in patients affected by intermittent claudication.
(7) The speed of flow and volume of flow of the lower extremities in patients with ischemia in the lower members.

Hereunder we expose the clinical results obtained after the administration during three months of the 2,4,6-triiodophenol in 200 cardiovascular patients.

Sick persons were divided in 4 groups; (1) 50 patients with cerebral vascular insufficiency, (2) 50 patients with coronary insufficiency, (3) 50 patients with hepatic insufficiency and (4) 50 patients with peripheral vascular insufficiency of the lower extremities. All these persons received an intramuscular administration, a dosage of 30 mg/day of 2,4,6-triiodophenol, carrying out controls at the first, second and third month of all angiohemodynamic parameters, supposing a total of 600 controls (150 per each group after the three months).

The obtained results are summarized in a statistical way in the following tables.

| | I - Structure: vascular wall. Action: Antiatherosclerotic. | | |
|---|---|---|---|
| | Variation (Δ %) | Postmedication | |
| Parameter | first month | 2nd month | 3rd month |
| DISTENSIBILITY PORTAL CAROTID AORTA | +17% | +27% | +30% |
| DISTENSIBILITY THORACIC AORTA | +7% | +11% | +14% |
| DISTENSIBILITY ABDOMINAL AORTA | +18% | +29% | +31% |
| DISTENSIBILITY CAVAL ILIAC ARTERY | +12% | +28% | +29,5% |
| | | average value | +26% |
| DISTENSIBILITY PORTAL VEIN | +15% | +29,5% | +32% |
| DISTENSIBILITY POST CAVAL SYSTEM | +7% | +12% | +15% |
| | | average value | +24% |

| | II - Structure: vascular surface. Action: vasodilatory. | | |
|---|---|---|---|
| | Variation (Δ %) | Postmedication | |
| Parameter | 1st month | 2nd month | 3rd month |
| VASCULAR CALIBER PORTAL CAROTID AORTA | +11% | +12% | +13% |
| VASCULAR CALIBER THORACIC AORTA | +3% | +7% | +9% |
| VASCULAR CALIBER ABDOMINAL AORTA | +6% | +11% | +13% |
| VASCULAR CALIBER CAVAL ILIAC ARTERY | +8% | +12% | +15% |
| VASCULAR CALIBER PORTAL SYSTEM | −13% | −23% | −26% |
| VASCULAR CALIBER POSTCAVAL SYSTEM | −9% | −14% | −13% |

| III - Function: Velocity. Action: Fluidifying + hemodynamizing. | | | |
|---|---|---|---|
| Parameter | Variation (Δ %) 1st month | Postmedication 2nd month | 3rd month |
| SPEED OF FLOW PORTAL CAROTID AORTA | +11% | +14 | +19 |
| SPEED OF FLOW THORACIC AORTA | +2% | +3 | +5 |
| SPEED OF FLOW ABDOMINAL AORTA | +3 | +5 | +7 |
| SPEED OF FLOW CAVAL ILIAC ARTERY | +7 | +11 | +14 |
| | | Average value | +11% |
| SPEED OF FLOW PORTAL SYSTEM | +16% | +21% | +29% |
| SPEED OF FLOW POSTCAVAL SYSTEM | +8% | +12% | +15% |
| | | Average value | +17% |

| IV - Function: waste Action: peripheral hyperemia. | | | |
|---|---|---|---|
| Parameter | Variation (Δ %) 1st month | Postmedication 2nd month | 3rd month |
| CEREBRAL MINUTE VOLUME | +23% | +27,6% | +34% |
| CARDIAC WASTE | +5% | +6% | +11% |
| LOWER EXTREMITY MINUTE VOLUME | +10% | +24% | +30% |
| HEPATIC MINUTE VOLUME (venous) | +24% | +16% | +23% |

| V - Function: Pressure Action: Hypotensor. | | | |
|---|---|---|---|
| Parameter | Variation (Δ %) 1st month | Postmedication 2nd month | 3rd month |
| SYSTEMIC ARTERIAL PRESSURE | −3% | −5% | −6% |
| PORTAL PRESSURE | −8% | −11% | −13% |

| VI - Cardiac contractility Action: inotropic effect. | | | |
|---|---|---|---|
| Parameter | Variation (Δ %) 1st month | Postmedication 2nd month | 3rd month |
| TELESYSTOLIC VOLUME | +8% | +11% | +13% |
| TELEDIASTOLIC VOLUME | −3% | −5% | −6% |
| EJECTION VOLUME | −9% | −8,4% | −8% |
| EJECTION FRACTION | −9,1% | −8,8% | −8,6% |

| VII - Function Fat in the blood Action: Hypocholesterinemic. | | | |
|---|---|---|---|
| Parameter | Variation ( 3) 1st month | Postmedication 2nd month | 3rd month |
| CHOLESTEROL | — | — | −15% |
| TRIGLYCERIDES | — | — | −12% |

CONCLUSIONS

The before mentioned values and results show that the 2,4,6-triiodophenol has a potent and efficacious ANTIATHEROSCLEROTIC action, improving considerably the parietal dynamic of all arteries (26%) and veins (24%). The product shows also an efficacious and potent FLUIDIFYING-HEMIDYNAMIZING action, as the speed of the sanguineous flow increased in 11% in the arteries and in 17% in the veins. Finally there could be found an efficacious and potent HYPEREMIANT action, increasing the volume of flow systemic circulatory minute (11%), cerebral (34%), hepatic (23%) and of the lower member (30%). The product subject of the invention does not produce any toxic effect or secondary effects of clinical importance in none of the patients after the three months administration. Besides it has been shown that the iodine concentration of the product does not alter the thyroid function.

EXAMPLE 3

Antiinflammatory Action (A) The antiinflammatory action is shown in white rats, of a weight of about 200–225 g, having provoked in these animals the leg oedema by means of an injection in the sole of the foot of 0.1 ml of a 1% Carrageenin solution.

One control group of ten animals, another the same medicated with indomethacin via oral at 30 mg/kg, in suspension in a carboxymethylcellulose solution, another group of ten rats, medicated with triiodophenol in oral solution at 5 mg/kg, another group medicated with trioodophenol at 1 mg/kg, injected via intramuscular and another group medicated with triiodophenol at 0.5 mg/kg via intramuscular. All medications are administered simultaneously to the formation of Edema.

The volume of the same is measured at 0 hours, 3 hours, 4 hours, 5 hours and 6 hours with a mercury Plestimograph.

The following Table indicates us the obtained average values:

| | 0 hours | 3 hours | 4 hours | 5 hours | 6 hours |
|---|---|---|---|---|---|
| Control group | 9 | 18,2 | 19,8 | 21,2 | 22 |
| Indomethacin 10 mg/kg oral. % inhibition | — | 59 | 63 | 69 | 73 |
| Triiodophenol 5 mg/ | — | 43 | 50 | 57 | 65 |

-continued

|  | 0 hours | 3 hours | 4 hours | 5 hours | 6 hours |
|---|---|---|---|---|---|
| kg oral. % inhibition |  |  |  |  |  |
| Triiodophenol 1 mg/ kg inj. % inhibition | — | 65 | 66 | 75 | 82 |
| Triiodophenol 0,5 mg/ kg inj. % inhibition | — | 20 | 42 | 49 | 60 |

(B) To a group of 10 rats of about 200–225 g is implanted at the dorsal zone, subcutaneously, balled cotton (about 9 mg) impregnated and afterwards dried with a solution of medicamentous substance and which amount is known.

We use as reference Dexamethasone and controls without medicament.

After 72 hours, once the animal is sacrificed, the granuloma formed around the implant is extracted and weighed, after drying at 100° C.

The antiinflammatory reduces the weight of the granuloma.

| Medicament | Dose per implant (micrograms) | % Reduction of the granuloma (Average) |
|---|---|---|
| Dexamethansone | 10 | 16 |
| " | 20 | 28 |
| " | 40 | 30 |
| Triiodophenol | 100 | 19 |
| " | 200 | 28 |
| " | 400 | 44 |

Analgesic action (A) To control analgesic activity we use mice of about 25 g by weight, in groups of ten mice, subjected to the test of the hot plate at 56° C.

Animals receive a medicamentous injection of 0.1 ml of solubilized aspirin with sodium bicarbonate, or of solubilized triiodophenol at pH 9'5.

Controls receive physiologic serum.

The time in which the animals indicate sensation of pain is measured with a chronometer.

In the hereunder table the results testing animals, 15 min. and 30 min. after the medication. Average values are taken of each group.

|  | 15 minutes | 30 minutes |
|---|---|---|
| Controls | 4,6 sec. | 4,6 sec. |
| Acetyl salicylic acid 500 mg/kg | 4,3 sec. | 6,8 sec. |
| Triiodophenol 10 mg/kg | 11,7 sec. | 11,8 sec. |
| Triiodophenol 1 mg/kg | 6,5 sec. | 6,7 sec. |

(B) "WRITHING SYNDROME" TEST

Irritant substance: acetic acid at 0.5% injected via intraperitoneal.

Foundation of the method consists in provoking a dolorous syndrome by pulling and torsion of the stomach and the hind legs of the animals.

These pullings or stretchings are calculated during a certain time, using it as the measure of the provoked ache.

Mice of about 22 g by weight were used, animals were left under abstinence during 24 hours before carrying out the test.

Mice were previously selected as to each individual response to the dolorous stimulus provoked by an intraperitoneal injection of 0.2 ml of an acetic acid aqueous solution at the 0.5%. Valid animals for realizing the test are those which respond within a margin of 15–35 pullings in about 5 to 15 minutes after the injection. The remaining animals are not useful.

PROTOCOL

Medication is realized via oral with the help of an esophageal cannula.

White lot: Administration of 0.1 ml of CMC 1% for each 10 g of corporal weight.

2,4,6-triiodophenol lot: Administration of 10 mg/kg of the product, suspended in CMC of 1%.

Aspirin-Lysin lot (Solusprin): Administration of 500 mg/kg aspirin, dissolved at 1%.

After medication, one has to wait 20 minutes for injecting 0.2 ml acetic acid of 0.5% via intraperitoneal, calculating the number of pullings during 5 minutes. After 60 and 100 minutes injection of acetic acid is repeated and pullings are calculated during 5 minutes.

RESULTS

The test was carried out in 9 mice in each lot.

|  | NUMBER ANIMALS | 20' | | 30' | | 100' | |
|---|---|---|---|---|---|---|---|
|  |  | TOTAL No. PULLINGS | % INHIB. | TOTAL No. PULLINGS | % INHIB. | TOTAL No. PULLINGS | % INHIB. |
| WHITE | 9 | 121 | — | 56 | — | 65 | — |
| 2,4,6-TRIIODO- PHENOL 10 mg/kg | 9 | 14 | 88,4 | 9 | 83,9 | 9 | 86,1 |
| ASPIRIN 500 mg/kg | 9 | 12 | 90 | 6 | 89,2 | 6 | 99,7 |

|  | 20' | | 30' | | 100' | |
|---|---|---|---|---|---|---|
| NUMBER ANIMALS | TOTAL No. PULLINGS | % INHIB. | TOTAL No. PULLINGS | % INHIB. | TOTAL No. PULLINGS | % INHIB. |

%Inhib.     2,4,6-triiodophenol 10 mg/kg —
            ASPIRIN              500 mg/kg - - -

| Summary of 175 clinic cases treated with 2,4,6-triiodophenol. | | | | | |
|---|---|---|---|---|---|
| DISEASES | TOTAL TREATED PATIENTS | % OBTAINED RESULTS | | | |
| | | E. | B. | R. | N. |
| VERTEBRAL ARTHROSIS | 56 | 83,33 | 10,42 | 6,25 | — |
| CERVICAL ARTHROSIS | 34 | 90,34 | 3,22 | 3,22 | 3,22 |
| LUMBAR ARTHROSIS | 4 | 50 | 25 | 25 | — |
| KNEE ARTHROSIS | 16 | 81,25 | 12,5 | 6,25 | — |
| HIP ARTHROSIS | 13 | 53,85 | 23,10 | 23,10 | — |
| OBLITERANT ARTHROSIS | 1 | 100 | — | — | — |
| CEREBRAL ATHEROSCLEROSIS | 37 | 81,25 | 6,25 | 9,35 | 3,15 |
| OBLITERANT ATHEROSCLEROSIS | 14 | 92,85 | 7,15 | — | — |

| TOTAL NUMBER OF TREATED PATIENTS | 175 |
|---|---|
| (E) EXCELLENT RESULT | 145 (82,86%) |
| (B) GOOD RESULT | 13 (7,43%) |
| (R) REGULAR RESULT | 14 (8,00%) |
| (N) NULL RESULT | 3 (1,71%) |

EXAMPLE 4

Preparation of tablets containing as active substance the 2,4,6-triiodophenol 1000 tablets containing each one 10 mg of 2,4,6-triiodophenol are prepared as follows:

| 2,4,6-triiodophenol | 10 g |
|---|---|
| microcrystalline cellulose | 185 g |
| Silica | 19 g |
| Magnesium stearate | 6 g |

The homogenized and compacted mixture is compressed to produce 1000 tablets of 0.22 g containing each one 0.09 g of active substance.

EXAMPLE 5

Preparation of gelatin capsules of No. 1 containing as active substance the 2,4,6-triiodophenol 1000 gelatin capsules containing each one 10 mg of 2,4,6-triiodophenol are prepared of:

| 2,4,6-triiodophenol | 10 g |
|---|---|
| microcrystalline cellulose | 55 g |
| Silica | 3 g |
| Magnesium stearate | 2 g |

The screened and homogenized mixture is introduced into the capsules, dosified at 70 mg in a suitable filling machine.

EXAMPLE 6

Preparation of 10,1 of syrup containing as active substance the 2,4,6-triiodophenol 10 l syrup containing 50 mg of 2,4,6-triiodophenol (each dose 5 ml) are prepared with the following components:

| 2,4,6-triiodophenol | 100 g |
|---|---|
| Lysin | 200 g |
| Saccharose | 7000 g |
| Glycerin | 500 g |
| Sodium chloride | 80 g |
| Methyl-p-hydroxybenzoate | 10 g |
| Isopropyl-p-hydroxybenzoate | 2 g |
| Sorbic acid | 10 g |
| Distillated water | necessary amount for 10 liters |

This syrup can be coloured and aromatized.

EXAMPLE 7

Preparation of 1000 injectable ampoules, containing as active substance the 2,4,6-triiodophenol 1000 injectable ampoules containing each one 10 mg of 2,4,6-triiodophenol are prepared with:

| | |
|---|---|
| 2,4,6-triiodophenol | 10 g |
| Lysin | 20 g |
| Sodium chloride | 35 g |
| Water for injectables | 5000 ml |

Sterlization is carried out and dosified at 5 ml.

What we claim is:

1. A method of treating a patient suffering from a disease selected from the group consisting of cerebral vascular insufficiency, coronary insufficiency, hepatic insufficiency, portal hypertension and chronic ischemia of the lower extremities, which comprises administering to said patient a therapeutically effective amount of a composition comprising 2,4,6-triiodophenol or pharmacologically acceptable addition salts thereof, in combination with a pharmaceutically acceptable carrier.

2. A method of treating a patient as claimed in claim 1, wherein the disease is cerebral vascular insufficiency.

3. A method of treating a patient as claimed in claim 1, wherein the disease is coronary insufficiency.

4. A method of treating a patient as claimed in claim 1, wherein the disease is hepatic insufficiency.

5. A method of treating a patient as claimed in claim 1, wherein the disease is portal hypertension.

6. A method of treating a patient as claimed in claim 1, wherein the disease is chronic ischemia of the lower extremities.

7. A method of treating a patient as claimed in claim 1, wherein 30 mg of said composition is administered to said patient per day.

8. A method of treating a patient as claimed in claim 1, wherein said composition is administered by intramuscular injection.

* * * * *